United States Patent [19]

Hill et al.

[11] Patent Number: 4,537,572
[45] Date of Patent: Aug. 27, 1985

[54] ASSEMBLY FOR POSITIONING A THERMOGRAVIMETRIC FURNACE

[75] Inventors: Harold I. Hill, Fairfield, Conn.;
Stanley D. Norem, Bayside, N.Y.;
Roger Targowski, Fairfield, Conn.

[73] Assignee: The Perkin-Elmer Corporation, Norwalk, Conn.

[21] Appl. No.: 576,292

[22] Filed: Feb. 2, 1984

[51] Int. Cl.³ ............... F27D 19/00; F27D 15/02; F27D 3/00
[52] U.S. Cl. ............................... 432/55; 374/14; 432/57; 432/81; 432/239
[58] Field of Search ............... 432/55, 57, 81, 239; 73/863.01, 863.11; 422/51, 307; 374/10, 14; 219/389; 261/DIG. 30

[56] References Cited

U.S. PATENT DOCUMENTS

| | | |
|---|---|---|
| 3,045,472 | 7/1962 | Paulik et al. ............... 422/51 |
| 3,055,206 | 9/1962 | Watson et al. ............... 374/14 |
| 3,666,252 | 5/1972 | Rice ............... 432/57 |

*Primary Examiner*—John J. Camby
*Attorney, Agent, or Firm*—F. L. Masselle; E. T. Grimes; J. D. Crane

[57] ABSTRACT

An apparatus for positioning a thermogravimetric furnace includes a furnace mounting bracket which is rotatable about and linearly translatable along a single axis. In addition, simultaneous rotational and linearly movement of the furnace is excluded.

15 Claims, 3 Drawing Figures

ASSEMBLY FOR POSITIONING A THERMOGRAVIMETRIC FURNACE

BACKGROUND OF THE INVENTION

The present invention generally relates to an assembly for positioning a thermogravimetric furnace and, in particular, relates to such an assembly having means for selectively moving the thermogravimetric furnace to either a sample loading position or a furnace cooling position.

Thermogravimetric analyzers are instruments designed to detect weight changes in a sample as it is subjected to preselected temperature changes. In general, such an analysis is carried out by first placing a sample in a sample tray which is suspended from one arm of a precision balancing mechanism. The sample is then introduced into a furnace the temperature of which is controllable and preselectable. Usually in such an analyzer, a portion of the furnace is movable and the sample tray is fixed, at least with respect to the movable portion of the furnace. The temperature of the furnace is then varied over time in a preselected fashion. This variation is generally referred to as a temperature profile and the weight of the sample is monitored throughout the profile. The most common method of analysis includes a continuous weight detection of the sample throughout the temperature profile. However, in some instances, only the weight of the residue at the end, usually at high temperatures, of the profile is of interest. In any event, the results of such an analysis are usually recorded via a chart recorder whereon the sample weight is plotted against the temperature during the profile.

In conventional thermogravimetric analyzers, after a temperature profile on a particular sample has been performed, the movable portion of the furnace is usually lowered away from the sample tray. This lowering is most frequently performed by manually grasping the lower portion of the furnace housing and moving it downwardly away from the suspended sample tray. This, of course, is extremely hazardous since the temperature of such furnaces can reach more than 1500° C. and such manual manipulation of the furnace can cause severe burns.

Another drawback common to conventional thermogravimetric furnaces is the prolonged time required for cooling the furnace before the next analysis can be performed. For example, since the furnace assembly reaches such high temperatures, which are usually at the end of the temperature profile, the cooling time between samples can be quite long. One common goal of analytical instrument designers is to have the total time of a sample analysis depend primarily on the actual analysis time plus the time required for changing samples. The present form of thermogravimetric analysis, due to the required cooling, entails considerable delays between samples.

SUMMARY OF THE INVENTION

Accordingly, it is one object of the present invention to provide an apparatus for positioning a thermogravimetric furnace which apparatus enhances safe operation and which is conducive to automation.

This object is accomplished, at least in part, by an apparatus having a furnace mounting bracket which is rotatably about and linearly translatable along a common axis.

Other objects and advantages will become apparent to those skilled in the art from the following detailed description read in conjunction with the appended claims and the drawing attached hereto.

BRIEF DESCRIPTION OF THE DRAWING

The drawing, not drawn to scale, includes.

DETAILED DESCRIPTION OF THE INVENTION

Figure 1:
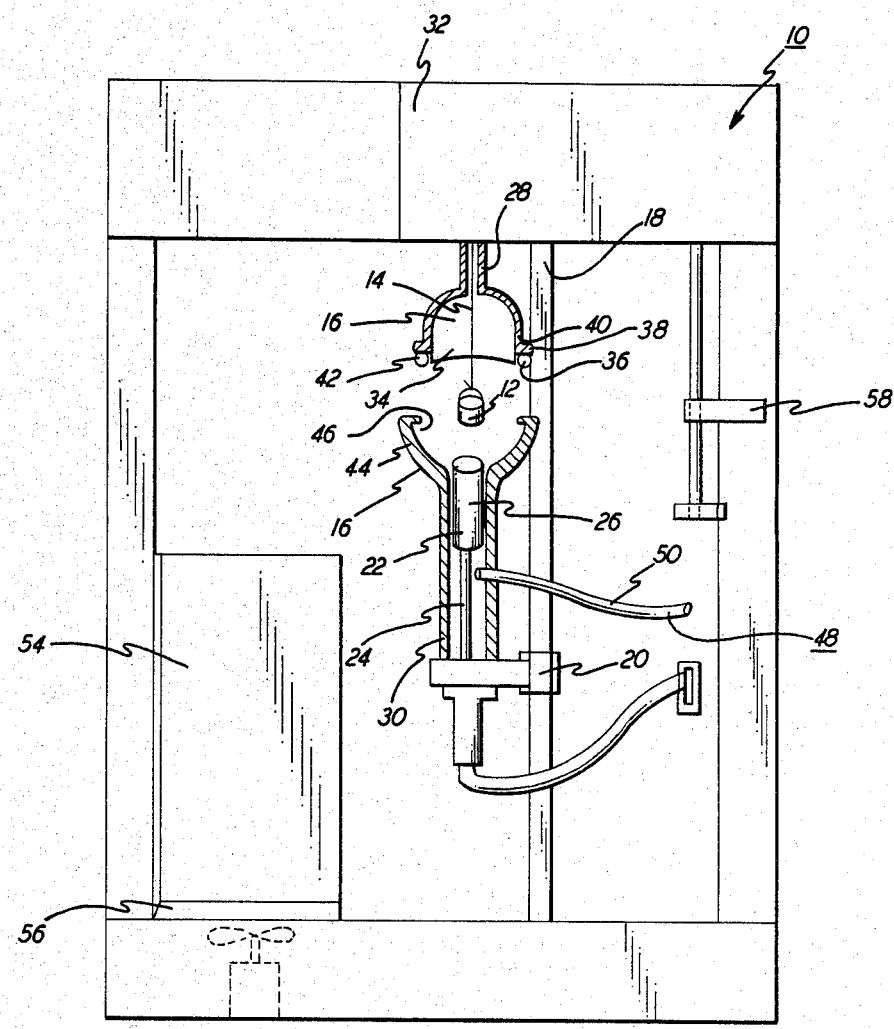
FIG. 1, which is a pictorial view of a thermogravimetric analyzer embodying the principles of the present invention.

A thermogravimetric analyzer, generally indicated at 10 in FIG. 1 and embodying the principles of the present invention, includes a sample tray 12 suspended from a wire 14 connected to one arm of a precision balance (not shown). The weight of the tray 12 is precisely calibrated and is a known factor which is compensated for within the measuring circuitry of the analyzer 10. The analyzer 10 also includes a segmented furnace assembly 16 affixed to a shaft 18 by means of a bracket 20.

In one embodiment, the furnace assembly 16 includes a furnace chamber 22 supported by, and thermally insulating from, a column 24, the chamber 22 preferably has an inside diameter larger than the largest outside dimension of the sample tray 12 whereby, when properly positioned, the sample tray 12 is within the furnace chamber 22. The furnace assembly 16 also includes heat providing means 26. In one example, the heat providing means 26 is in the form of an electrical heating mechanism connected to an externally positioned frame mounted connector and passing through the furnace chamber support column 24. The connection is adapted to permit both vertical and rotational movement of the furnace without binding. For example, the connecting wires are provided with enough slack so that the extreme positions of the furnace assembly 16 can be reached without undue strain being applied thereto. The furnace assembly 16 preferably, includes an upper portion 28 and a lower portion 30 each of which is formed from a high temperature glass, for example, quartz.

The upper portion 28 is fixedly attached to the frame 32 of the analyzer 10 and extends downwardly toward the lower portion 30 of the furnace assembly 16. In one embodiment, the upper portion 28 includes a hemispheric opening 34 at one end 36 thereof which hemispheric opening 34 includes an external protrusion 38 about the periphery 40 thereof. Abutted against the external protrusion 38 and distal from the frame 32 an O-ring 42 is provided to establish a seal with the lower portion 30 of the furnace assembly 16 when the lower portion 30 is urged thereagainst.

The lower portion 30 of the furnace assembly 16 includes a hemispheric opening 44 at one end 46 thereof proximate the upper portion 28. The hemispheric opening 44 is complementary to the hemispheric opening 34 of the upper portion 28. The lower portion 30 is hollow and extends about the furnace chamber 22 in a generally cylindrical fashion. The lower portion 30 is provided with a means 48 for controlling the atmosphere under which the analysis is carried out. In one embodiment, the means 48 includes a gaseous conduit 50 which is affixed to and penetrates into the lower portion 30 furnace assembly 16. The conduit 50 allows controlled gaseous communication between the interior of the furnace assembly 16 and a source of gas, not shown in the drawing. Preferably, an electronically controllable valve is provided in the conduit via which the atmosphere within the furnace is remotely controllable by, for example, a switch or by a software command.

The analyzer 10 further includes a cooling closet 54 sized to accept the lower portion 30 of the furnace assembly 16 therein. The closet 54 includes a screened floor 56 through which a coolant, for example air, can be circulated, via, for example, a fan, about the lower portion 30 of the furnace assembly 16 when positioned therein.

A sample loading platform 58, adapted to be rotatably positioned beneath or near the sample tray 12, is rigidly affixed to a rod 61 rotatably affixed to the frame 32 of the analyzer 10. The platform 58 includes means 60 for preventing the lower portion 30 of the furnace assembly 16 from engaging the upper portion 28 when the platform 58 is in an active position.

Figure 2:
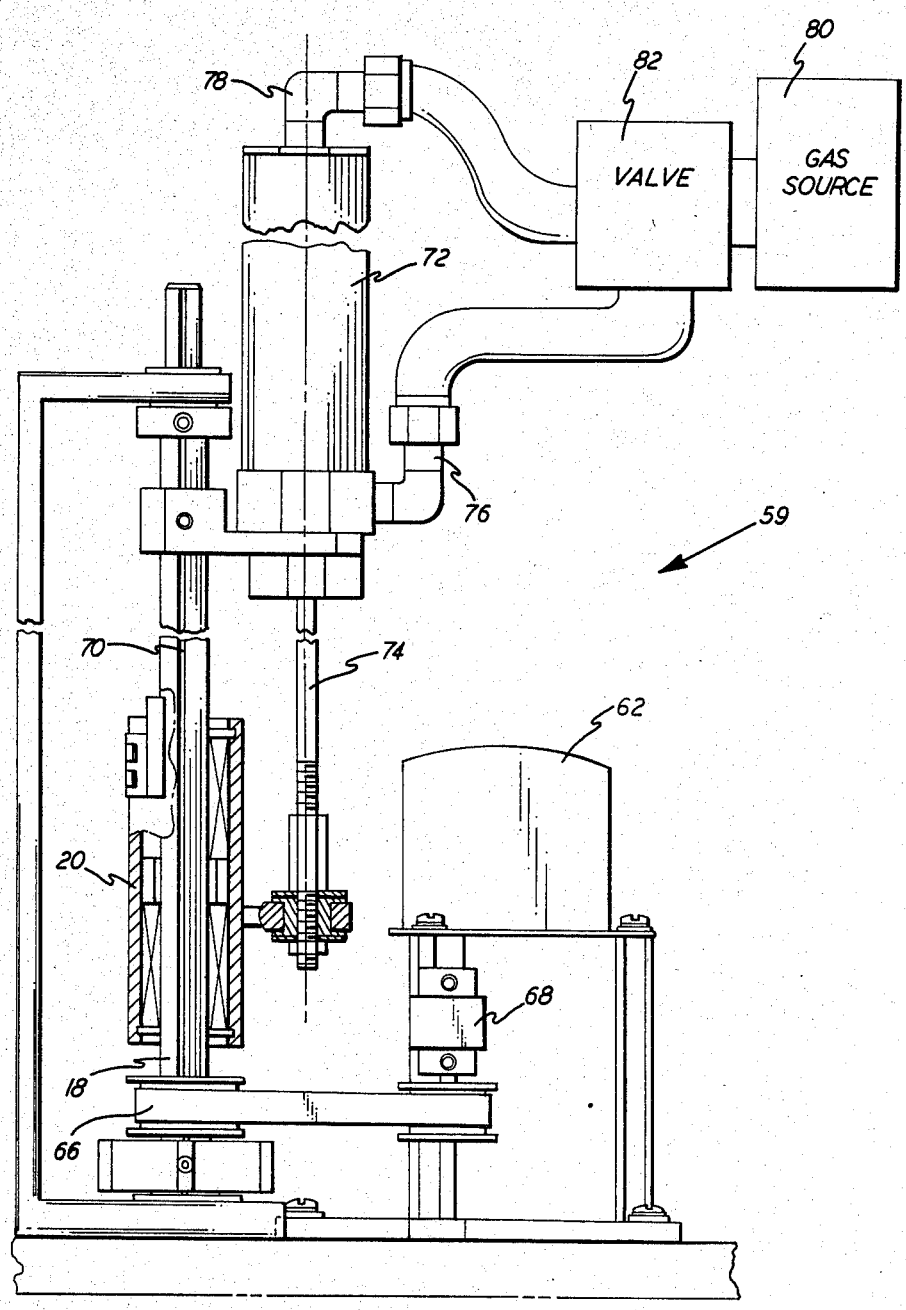
FIG. 2, which is a pictorial view of a control mechanism of the analyzer of FIG. 1.

Referring specifically to FIG. 2, there is shown therein an assembly, generally indicated by the numeral 59, for positioning the lower portion 30 of the thermogravimetric furnace assembly 16. The assembly 59 includes an electric motor 62 interfaced with the shaft 18 upon which the lower portion 30 of the furnace assembly 16 is rigidly affixed by means of the bracket 20. The interface includes a rotational torque transfer means 66 and a slip clutch 68 via which excess rotational force transferred to the shaft 18 is disengaged therefrom when the shaft 18 is located in a preselected position. Preferably, the shaft 18 includes a longitudinal groove 70 therein which, when the bracket 20 is attached thereto, prevents rotational movement of the bracket 20 with respect to the shaft 18.

The shaft 18 also carries a bi-directional pneumatic cylinder 72, which bi-directional pneumatic cylinder 72 is affixed to the furnace bracket 20 via the piston rod 74 thereof. Thus, the pneumatic cylinder 72 is adapted to move the bracket 20 along the shaft 18 in a vertical direction in response to pneumatic pressure applied at either a first or a second port, 76 or 78 respectively, thereof.

The first and second ports, 76 and 78 respectively, hereinafter referred to as the furnace raising port 76 and the furnace lowering port 78, respectively, are connected to a source 80 of compressed gas via a switch valve 82. The switch valve 82 is adapted to direct pressurized gas to either selected port 76 or 78, of the pneumatic cylinder 72. In the preferred embodiment, the switch valve 82 is of a type which is controllable via an electronic command.

As apparent from the above description the preferred assembly 59 employs two different motive sources for the manipulation of the lower portion 30 of the furnace assembly 16. That is, an electric motor 62 is employed for the rotational movement of the shaft 18 whereas a bi-directional pneumatic cylinder 72 is employed for the linear translation of the bracket 20 along the shaft 18. This arrangement is selected for its mechanical simplicity and is not considered to exclude the use of other motive means for either movement.

For the following description of a typical operation of the present analyzer it is initially assumed that a particular analysis has just been completed. The lowering port 78 of the pneumatic cylinder 72 is pressurized and the electric motor 62 is energized upon the pneumatic cylinder 72 extending a preselected distance. The movement of the cylinder 72 detaches the lower portion 30 from the upper portion 28. Next, the rotation of the shaft 18 caused by the electric motor 62 carries, in this example, the lower portion 30 of the furnace assembly 16 into the cooling closet 54 whereupon the cooling fan is activated.

Under these conditions, the sample loading platform 58 can be swung out of its storage position and positioned beneath the sample tray 12. The use of the platform 58 is optional although it is preferably used to prevent sample material which may overflow the sample tray 12 from falling into an operator inaccessible position. After the sample has been placed into the sample tray 12, the platform 58 must be swung back to the storage position prior to any vertical movement of the lower portion 30 of the furnace assembly 16. With the platform 58 returned to the storage position, the electric motor 62 can be energized to rotate the lower portion 30 of the furnace assembly 16 beneath the upper portion 28 and in alignment herewith. In the automatic mode, the furnace assembly 16, upon reaching a rotational stop, causes the slip clutch 68 to remove torque from the shaft 18 and is then raised by the pneumatic cylinder 72 the preselected distance, with the preselected force, to engage the upper portion 28 and form a seal with the O-ring 42 thereof. When the lower portion 30 is engaged with the upper portion 28 the sample tray 12 is located within the furnace chamber 22 and a thermogravimetric analysis can be carried out.

Upon completion of the analysis, the lower portion 30 is again lowered away from the upper portion 28 of the furnace assembly 16. Preferably, if so desired, the lower portion 30 of the furnace assembly 16 can be maintained beneath the upper portion 28 until the next sample is prepared. One instance where the lower portion 30 would not need to be cooled, via rotation into the cooling closet 54, is when the next analysis involves temperatures which are relatively high and near the end of the temperature profile. Another such instance is under conditions where the next sample is "fluffy" and any air currents are to be avoided.

In such an instance, upon completion of the sample loading, the lower portion 30 of the furnace assembly 16 is raised to engage the upper portion 28. As an alternative, depending on the analysis being performed, the furnace, upon reaching its lowest position, can be rotated into the cooling closet 54 and the temperature thereof brought to an acceptable reduced temperature.

Figure 3:
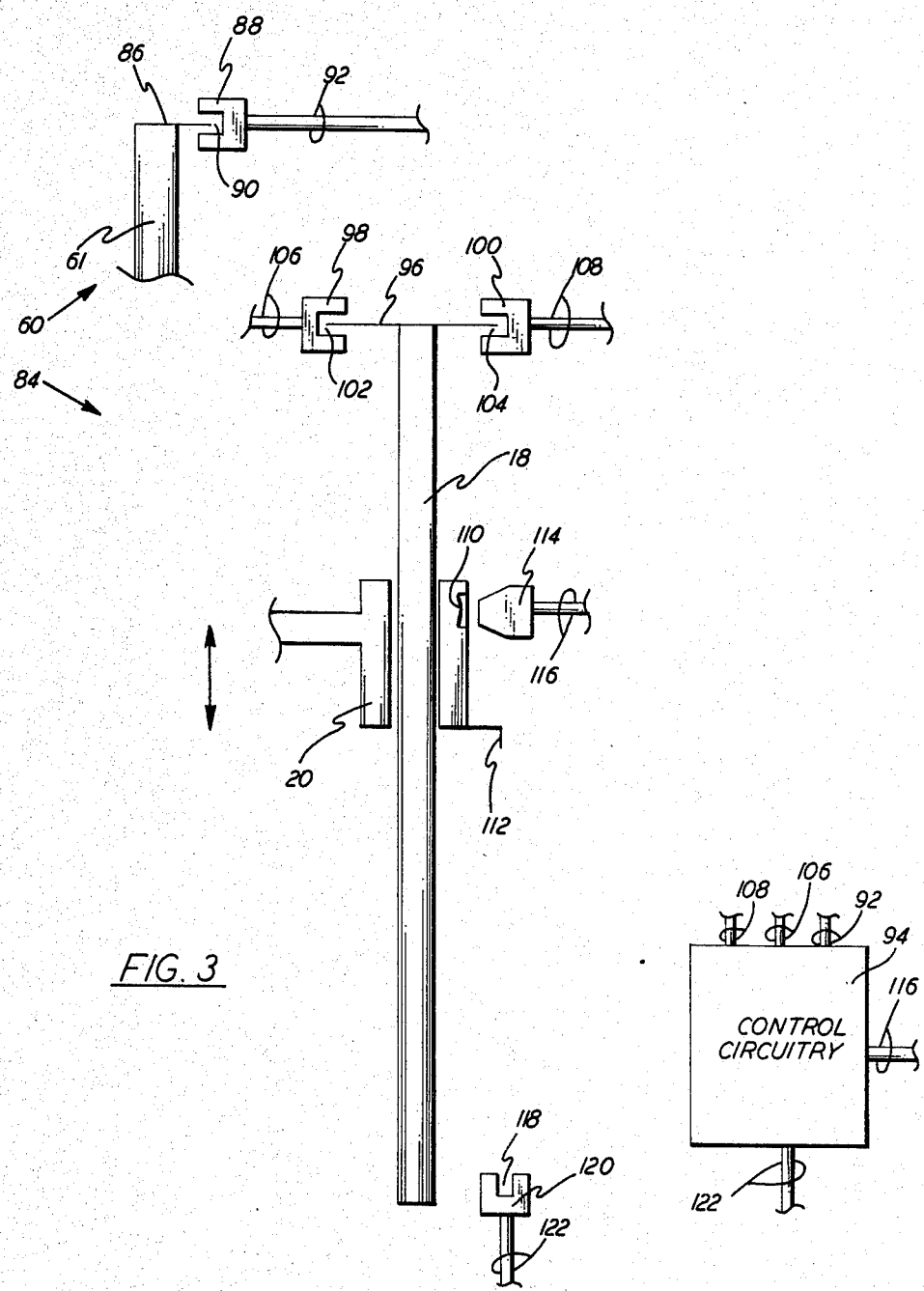
FIG. 3, which is a schematic diagram of a control circuit for the analyzer shown in FIG. 1.

Referring specifically to FIG. 3, a preferred position control circuit, generally indicated at 84, is depicted. As shown, the sample platform rod 61 includes a flag 86 which flag 86 is rigidly affixed thereto and rotates therewith. In addition, the means 60 includes a position sensor 88 having a gap 90 through which the flag 86 rotates. The leads 92 of the sensor 88 are connected to a control circuit 94 which includes logic circuitry adapted to control the movement of the lower portion 30 of the furnace assembly 16. That is, when the sample tray 58 is rotated beneath the tray 12 movement of the lower portion 30, by means of the control circuitry 94, is prevented based on the signal from the sensor 88.

Further, as shown in FIG. 3, the shaft 18 carries a flag 96 thereon which rotates therewith. The flag 96 is cooperatively arranged with two position sensors, 98 and 100, thereof. The leads, 106 and 108, of the sensors, 98 and 100, respectively, are connected to the control circuitry 94. By these inputs the control circuitry 94 "recognizes" the rotational position of the shaft 18 and thus the lower portion 30 of the furnace 16.

The linear translation of the bracket 20 along the shaft 18 is controlled by a first bracket flag 110 which is a light reflective target and a second bracket flag 112 which protrudes downwardly below the bottom plane of the bracket 20. The presence or absence of the first bracket flag 110 is sensed by a reflection sensor 114. The presence of the flag 110 in the plane of the reflection sensor 114 being indicative that the lower portion 30 of the furnace 16 is engaged to the upper portion 28 thereof. This data is carried to the control circuitry 94 via leads 116. When the lower portion 30 is fully lowered the downwardly protruding flag 112 penetrates the gap 118 of sensor 120 whereby this information is conveyed to the control circuitry 94 via leads 122. Once, the flag 112 is sensed by sensor 120 the lower portion 20 is allowed to rotate into the cooling closet 54.

In the preferred embodiment, the sensors, 88, 98, 100 and 120 are TIL138 source and sensor assemblies manufactured and marketed by Texas Instruments Inc. Dallas, Tex. The reflective sensor 114 is preferably a TIL139 assembly, also marketed and manufactured by Texas Instruments.

One advantage of the analyzer 10 is that the operator is no longer required to manually manipulate the lower portion 30 of the furnace assembly 16. As a consequence, the hazard regarding burns is effectively eliminated. Another advantage is that the time between consecutive analyses, due to the availability of cooling the lower portion 30 of the furnace assembly 16, is less dependent on furnace cooling and thus more dependent on sample delivery time to the sample tray. This greatly improves the efficiency of the analyzer 10, especially for example, when a plurality of different samples are to be tested or a plurality of different tests are to be performed on a single type sample.

Although the present invention has been described herein with respect to a specific embodiment, other arrangements and configurations will become apparent to those skilled in the art upon reading this description. Consequently, the embodiment described herein is considered exemplary only and is not deemed limiting. The present invention is thus deemed limited only by the appended claims and the reasonable interpretation thereof.

What is claimed is:

1. Apparatus for positioning two halves of a thermogravimetric furnace, said apparatus comprising, in combination:
   a first portion of a thermogravimetric furnace disposed at a fixed location;
   a rotatable shaft;
   means affixing a second portion of a thermogravimetric furnace such that said second portion rotates about the axis of said shaft when it rotates and said affixing means is longitudinally displaceable along said shaft;
   moving means coupled to said affixing means to longitudinally displace said second portion relative to said shaft between a first position where said first portion and said second portion fit together to form an oven enclosure;
   rotating means to rotate said shaft between two positions, the first position comprising a cooling position and the second position comprising an engaging position whereat said moving means may be actuated to cause said first and said second portion to fit together;
   means for excluding simultaneous rotation of said shift and longitudinal displacement of said affixing means.

2. The apparatus of claim 1 wherein said rotating means includes an electric motor and includes means to limit the extent of rotation to between said two positions.

3. Apparatus as claimed in claim 2 wherein said means for controlling the extent of rotation includes a slip clutch.

4. Apparatus as claimed in claim 2 further comprising:
   means for limiting the extent and velocity of said linear translation.

5. Apparatus as claimed in claim 4 wherein said limiting means including a pneumatic piston interconnected with said furnace portion affixing means.

6. Apparatus as claimed in claim 5 wherein said pneumatic piston is bi-directionally translatable within a cylinder having a pneumatic input at each end thereof.

7. Apparatus as claimed in claim 1 further comprising:
   means for limiting the extent and velocity of said linear translation.

8. Apparatus as claimed in claim 7 wherein said limiting means including a pneumatic piston interconnected with said furnace portion affixing means.

9. Apparatus as claimed in claim 5 wherein said pneumatic piston is bi-directionally translatable within a cylinder having a pneumatic input at each end thereof.

10. Apparatus as claimed in claim 1 wherein said excluding means includes a plurality of position sensors each of which provides an electrical signal indicative of the presence or absence of said furnace portion affixing means at a plurality of specific positions.

11. Apparatus as claimed in claim 10 wherein two of said plurality of sensors are indicative of the rotational position of said furnace portion affixing means whereby linear translation is inhibited at one rotation limit and uninhibited at the other rotational limit.

12. Apparatus as claimed in claim 11 wherein two of said plurality of sensors are indicative of the linear translation position of said furnace portion affixing means along said shaft whereby rotation of said shaft is inhibited at one linear translation limit and uninhibited at the other linear translation limit.

13. Apparatus as claimed in claim 10 wherein two of said plurality of sensors are indicative of the linear translation position of said furnace portion affixing means along said shaft whereby rotation of said shaft is inhibited at one linear translation limit and uninhibited at the other linear translation limit.

14. Apparatus as claimed in claim 1 further comprising means for cooling said second furnace portion when said shaft is at its cooling position.

15. Apparatus as claimed in claim 14 wherein said cooling means is activated as a result of a signal indication of the rotational position of said shaft.

* * * * *